United States Patent [19]
Biegel et al.

[11] Patent Number: 4,774,415
[45] Date of Patent: Sep. 27, 1988

[54] DEVICE FOR STERILIZATION OF A HOSE COUPLING DEVICE IN THE CONNECTED CONDITION

[75] Inventors: Hubert Biegel, Tholey-Theley; Wolfram Weber, Spiesen-Elversberg; Arthur Meisberger, St. Wendel; Bernd Mathiew, Spiesen/Elversberg, all of Fed. Rep. of Germany; Wolfram Weber, Spiesen-Elversberg; Arthur Meisberger, Wendel; Bernd Mathieu, Spiesen/Elversberg, all of Fed. Rep. of Germany

[73] Assignee: Fresenius AG, Bad Homburg, Fed. Rep. of Germany

[21] Appl. No.: 4,502

[22] Filed: Jan. 20, 1987

[51] Int. Cl.$^4$ .......................... A61L 2/10; G21K 5/04; H01J 37/20
[52] U.S. Cl. ............................ 250/455.1; 250/494.1; 250/495.1; 250/504 R
[58] Field of Search ............ 250/492.1, 432 R, 504 R, 250/495.1, 428, 429, 455.1; 374/121, 130, 126

[56] References Cited
U.S. PATENT DOCUMENTS

| | | | |
|---|---|---|---|
| 3,227,877 | 1/1966 | Dreyfus | 374/130 |
| 4,412,134 | 10/1983 | Herold et al. | 250/455.1 |
| 4,433,244 | 1/1984 | Hogan | 250/455.1 |

FOREIGN PATENT DOCUMENTS

| | | | |
|---|---|---|---|
| 1936245 | 2/1971 | Fed. Rep. of Germany | 250/504 |
| 8604674 | 8/1986 | World Int. Prop. O. | 374/126 |

Primary Examiner—Bruce C. Anderson
Assistant Examiner—Paul A. Guss
Attorney, Agent, or Firm—Todd S. Parkhurst

[57] ABSTRACT

The device in accordance with the invention for the sterilization of a hose coupling device (in its connected condition) of dialysis apparatus, comprises an opening housing into which the coupling device is placed. The coupling device is subjected to infrared radiation from heating elements in the housing whose heating effect is monitored and automatically controlled by a temperature probe arranged under the coupling device in the housing. Since the temperature probe is designed to have such an infrared absorption characteristic that the temperature increase rate of the probe is substantially the same as that of the coupling device, one may be certain that the coupling device will have reached the desired temperature (which is detected at the temperature probe) with only a slight delay if any. At the same time there is the advantage that the interior of the coupling device is heated to substantially above the minimum necessary sterilization temperature.

10 Claims, 2 Drawing Sheets

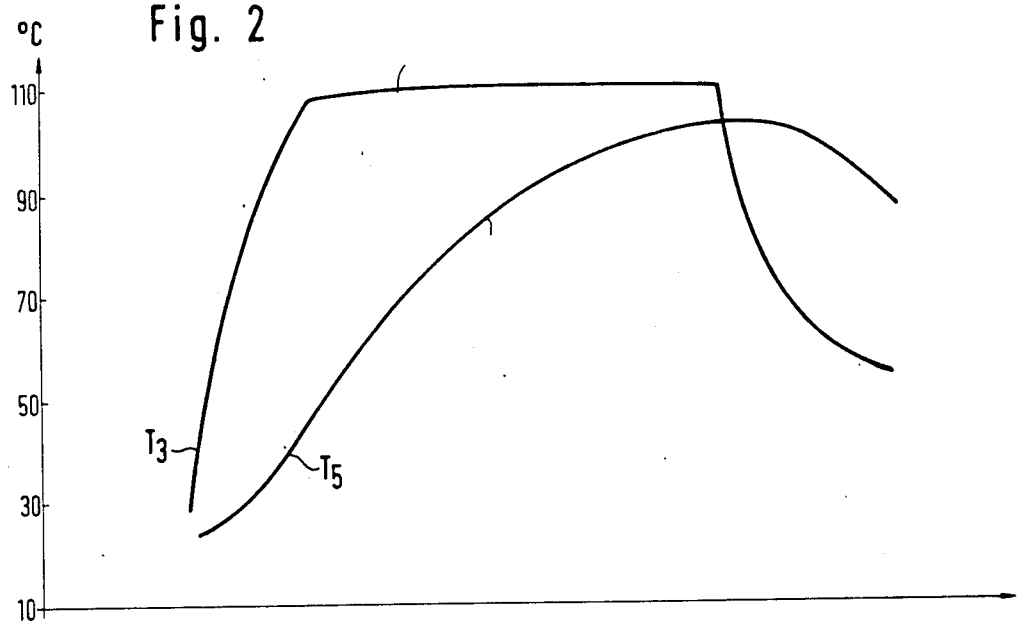
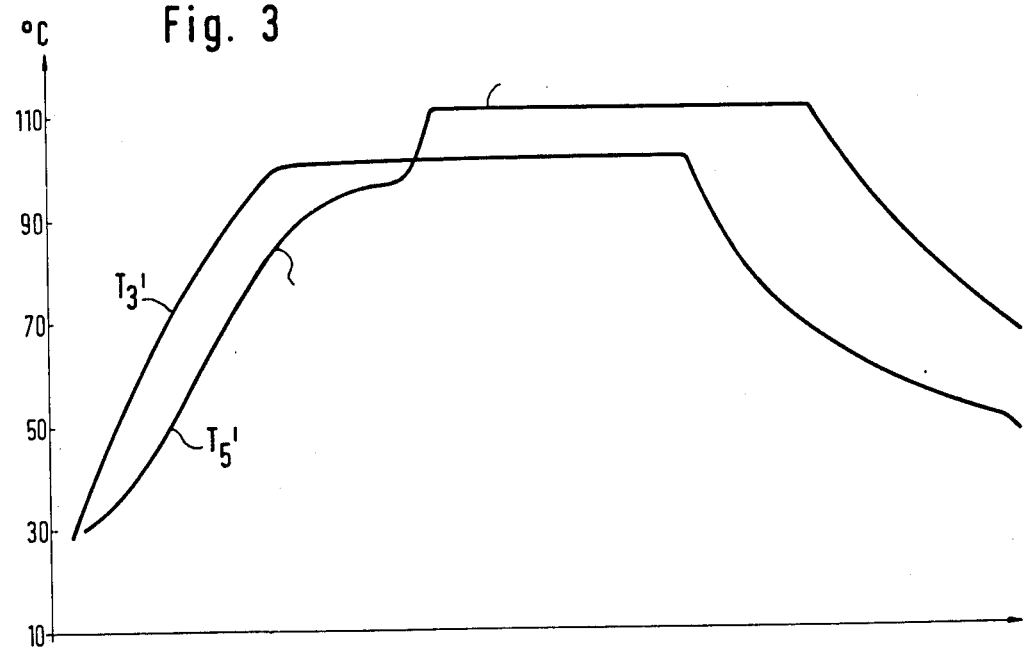

DEVICE FOR STERILIZATION OF A HOSE COUPLING DEVICE IN THE CONNECTED CONDITION

BACKGROUND OF THE INVENTION

The invention relates to a device for the sterilisation of a hose coupling device in the coupled condition thereof for medical purposes, comprising a housing able to be opened and defining an interior space, at least two infrared radiation sources, preferably in the form of halogen lamps, which are arranged in the interior of the housing, a holding means for locating the coupling device in the interior of the housing, a temperature probe arranged in the interior of the housing under the coupling device, and a controller which is connected with the temperature probe in order to automatically maintain the temperature in the interior of the housing at a given, preset value.

A device for the sterilisation of a coupling device in the connected state has been previously proposed having an opening and closing housing with an interior space in which at least two infrared radiation heat sources, more specially in the form of halogen lamps, were arranged. In order to support the hose coupling device, the known structure had a holding device in which the hose coupling was placed so that it was completely within the interior of the housing when the same was closed.

The previously proposed device further housed a temperature probe which was arranged under the hose coupling device and was connected with a controller for automatically keeping the temperature in the interior of the housing at a given value on the basis of the output signal of the temperature probe. When the temperature probe produces a given output signal, the radiation heat sources were so switched back that the desired temperature was maintained in the interior space.

However the previous device suffered from the disadvantage that the low thermal capacity of the temperature probe meant that it reached the given temperature level substantially more rapidly than the coupling device itself, since it had generally the same thermal absorbency as the coupling device. This in turn meant that the automatic controller decreased the power fed to the radiation heat sources with the effect that the coupling device itself only reached the necessary temperature of approx. 100° C. (as needed for the sterilisation of coupling devices) after a certain delay had elapsed. The maintenance of this temperature is however of crucial importance, since such devices are used for the sterilisation of coupling devices used in peritoneal dialysis equipment. Accordingly the desired, set temperature has to be reached at all costs, as there would otherwise be no guarantee that possible microbial contamination of the hose coupling device would be eliminated, and failure to provide for effective sterilisation would in fact lead to the risk of peritonitis.

Furthermore the previously proposed device had the disadvantage that a substantially longer period of time had to elapse before attaining the given coupling device temperature and this further involved an increased consumption of energy.

SHORT SUMMARY OF THE INVENTION

Taking this prior art into account one object of the invention is to so improve a device of the above-mentioned type for the sterilisation of a coupling device in the coupled state that with a shorter heating up time one may be certain that the coupling device attains the temperature needed for sterilisation.

In order to achieve these or other objects appearing herein the temperature probe has such an IR radiation absorption characteristic that it is substantially only heated by the convection air.

The outcome of this is that the temperature increase curves (or temperature rate of increase curves) of the temperature probe and of the coupling device, respectively, are so nearly indentical that there are only minor and insubstantial differences in the actual temperature levels of the probe and of the coupling device. In fact, investigations carried out as the present invention was being evolved indicated that when a temperature probe constructed in accordance with the invention is used its rate of temperature increase curve, like the rate of temperature increase curve of the coupling device, is essentially linear and has more or less the same slope as the curve of the coupling device.

The effect is then even that, if the air temperature is held constant, as for example at a level of 120° C. in the interior of the housing, such temperature being indicated, the temperature within the liquid duct in the coupling device will be far in excess of 120° C., since the water in the duct is more intensely heated owing to its distinctly higher IR absorption capacity. In fact the surface of the coupling device is practically cooled by the hot air at 120° in the interior of the housing, whereas in the duct or lumen there will be a higher temperature than at the outer surface. Accordingly, in contrast to the known device, one may be certain of such a pronounced heating effect on the coupling device in every case that it is effectively sterilized.

A further useful effect provided by the invention is that the time for attaining the necessary sterilisation temperature may be substantially curtailed, something that will also have a favorable effect on the energy or power consumption of the device in accordance with the invention.

Further useful developments of the invention are defined in the claims.

The temperature probe used in accordance with the invention is preferably characterized by being so designed that the coupling device is essentially only heated by the air maintained in a circulating convection current. Consequently it essentially does not absorb the IR radiation issuing from the IR radiation source, the probe either reflecting the radiation or allowing it to pass through it. For reasons of economy the reflecting form is preferred, in which the IR radiation issuing from the radiation sources (with a wavelength of 0.8 to 50 microns) is reflected with generally zero absorption.

The wording "generally zero absorption" is to be understood in connection with the present invention to mean a degree of reflection or reflectivity of at least 75% and more especially of at least 85%.

The desired thermal behavior of the temperature probe may with especial advantage be by the provision of such surface with good IR reflecting properties, which with advantage may be a metallic surface. The metals which may be used for this purpose include silver, aluminum and the like. It is preferred for them to have a highly polished surface.

Further advantages may be achieved as regards the heating up time if the wall of the interior of the housing is reflecting so that the thermal radiation may be practically focused on the coupling device. For this purpose it is also possible to have a metallic coating on the inner wall surface of the interior.

It is furthermore an advantage if the coupling device used in the device of the invention is made of a thermally resistant resin transparent to IR radiation. This enables the aqueous solution in the coupling device to be heated to such a temperature by the IR radiation that it is also in the interior of the coupling device and of the lumen of the hose adjacent thereto that the germicidal effect is produced. The temperature reached in the hose and the coupling device, respectively, may in this case be higher than the temperature attained in the interior of the device of the invention owing to convection, and which for example may be about 120°.

In order to prevent evaporation of the heated liquid solution it is therefore necessary to have hose clamps or clips both on the input and the output sides of the device so that between the clips the aqueous solution in the lumen of the hose and in the coupling device may be held up to a gage pressure of 3 bar. Owing to this temperatures of 125° C. and more may be attained in the clipped section of the duct without damage to the hose or to the coupling device.

The clips may be in the form of loose clamps or of clamping fittings secured directly in the wall of the housing. It is an advantage if they are so designed that they are operated by closing the housing lid.

Synthetic resins for the construction of the coupling device which are substantially transparent to IR radiation include for instance polyesters (such as polybutylene terephthalate) or polycarbonate, at least one of the said coupling device halves being transparent to IR radiation. Such synthetic resins are thermally resistant up to at least 150° C.

Further details of construction, teachings and beneficial effects of the invention will be gathered from the following description of one working example thereof with reference to the drawing.

LIST OF THE SEVERAL FIGURES OF THE DRAWINGS

FIG. 2 is a graph of temperature against time in the case of a prior art device.

FIG. 3 is a graph of temperature against time applying for the device of the invention.

DETAILED DESCRIPTION OF WORKING EXAMPLE OF THE INVENTION

Figure 1:
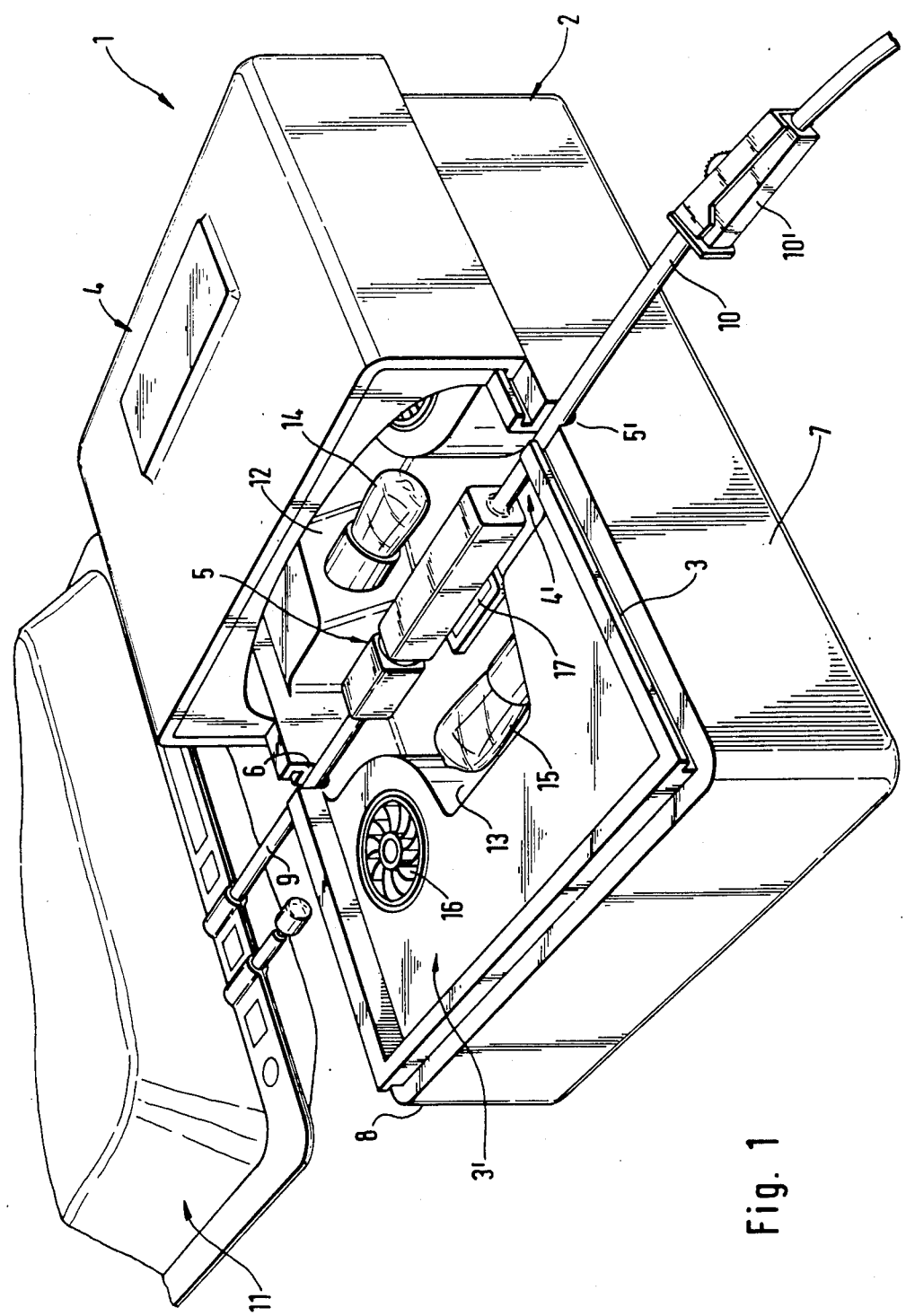
FIG. 1 is a perspective pictorial view of the embodiment of the invention in a partly opened state.

Turning firstly to FIG. 1 it will be seen that the device of the invention has a housing 2, which is provided with two lids or covers which slide along a rail 3, only the cover 4 being shown, while the other cover, which is of like construction, has been omitted from the figure. The two covers are provided with a catch, not illustrated, so that they are locked and not able to be opened unintentionally after being shut when sterilisation is in progress.

The housing 2 has an interior, which in turn has a holding means for the coupling device 5. In the present example the holding means includes two recesses 5' and 6 provided in parallel housing walls 9 and 10, respectively, and in which the hose parts 9 and 10, respectively, may be placed. The hose parts 9 and 10 are connected with a hose coupling device 5. Furthermore the part of the hose 9 is joined to a sac 11 containing a flushing or dialysis solution, whereas the other piece 10 of hose runs through a clamp 10' to the patient.

It is an advantage if the housing 2 has at least one further clip making it possible for the piece of hose 10 and possibly also the hose 9 to be shut off in such a way as to resist a hose internal gage pressure of up to 3 bar. For this it is possible to have one or two such clips on the two sides of the coupling device which are so arranged on the housing 2 that they are able to grip and effectively nip the hose pieces 9 and 10 when they are in the housing.

On the other hand it is however possible for at least one of the two recesses 5' and 6 to be designed as a clip in such a way that when the hose end 10 is laid in the recess it will be clipped by the housing lid.

Since the sac 11 normally has a frangible part (not illustrated) at the point of transition to the hose end 9 and such frangible part has to be broken before the contents of the sac are able to flow towards the coupling device, it is sufficient if there is a clipping means 10' or recess 5' on the side of the housing 2 further from the the sac 11.

As indicated in FIG. 1, the coupling device 5 is so kept in place by the holding means in the housing 2 that the entire coupling device 5 assumes a position in the interior. The latter has two opposite recesses 12 and 13 or wells in which respective IR radiation sources 14 and 15 are positioned and which are preferably in the form of halogen lamps. The radiation sources 14 and 15 are supplied with power in a conventional manner, which is not illustrated.

The reader will further be able to see that a blower 16 is provided in order to cool the interior before the removal of the coupling device 5 after sterilisation.

Under the coupling device 5 there is temperature probe 17 in the interior. This probe is connected by means which are not shown with an automatic controller to set the temperature in the interior at a predetermined or given level. The automatic controller may be of conventional design and accordingly will be understood without further description.

The temperature probe 17 of the device 1 of the present invention has such an IR light absorption characteristic that the temperature increase rate of the temperature probe 17 is essentially the same as the temperature increase rate of the coupling device 5. This is achieved in the present working example by an arrangement in which the temperature probe 17 is substantially only heated by convection, that is to say by the heated air in the interior, for which purpose the temperature probe 17 is provided with a high reflectivity surface, i.e. one reflecting as much of the incident radiation as possible. Such good reflecting properties may be produced by having a metallic coating which may also be present on the inner wall faces of the entire interior and the recesses 12 and 13, something which leads to the further useful effect that the efficiency of the device 1 may be substantially increased and it is then possible to have a lower temperature of the outer face of the housing.

When a coupling device 5 is to be sterilized, the first step is for the two halves of the coupling device to sprayed with a little disinfectant and then fitted together. Then the device 1 is opened by sliding the two lid halves to such a degree that the connected coupling device 5 may be placed in the interior in the manner shown in FIG. 1. After this the housing 2 is shut. After switching on the power supply for the radiation sources 14 and 15 the heating operation will start, while at the same time a means (not shown) is operative which responds to any attempted opening of the housing 2.

When a predetermined sterilisation temperature has been attained, as will be detected by the temperature probe 17, the supply of power to the radiation sources 14 and 15 is so decreased by automatic control that the temperature reached in the interior will be maintained.

The above mentioned matching of the temperature increase rates of the temperature probe 17 and of the coupling device 5, ensures that the coupling device 5 attains the necessary sterilisation temperature, there being the advantage that there is a higher temperature level in the interior of the coupling device 5 than on its surface, this making a further contribution to the reliablity of the sterilisation operation.

It is to be noted in this connection that the coupling device half joined to the piece 10 of hose and which is on the patient side of the device will contain spent fluid at the time it is joined to the other coupling device half. Such fluid will not escape owing to the low pressure in the abdominal cavity but the fluid will extend as far as the end of the coupling device half. At the time of connection of the two coupling device halves the piece of hose 9 is shut off by the frangible part so that it will be a question of a sealed space filled with fluid. This fluid has very high IR radiation capacity so that the heating effect in the chamber or interior on the fluid duct will cause temperatures far in excess of 120° to be reached and this will ensure that sterilisation is fully effective.

The coupling device halves on the other hand will be less heated, since at least one of them is made of a thermally resistant synthetic resin transparent to IR radiation.

Preferred materials in this respect are polyesters such as polybutylene terephthalate and polycarbonate.

After the sterilisation time, which is also preset, has elapsed, the blower 16 is switched on and so cools the interior to the temperature at which the coupling device 5 is to be removed and the lid locking means will be inactivated so that the housing may be opened again.

FIG. 2 shows a graph of temperature plotted along the vertical axis against time (horizontal axis) applying for a known device to make clear the distinct spacing out of the two temperature curves, that is to say of the curve $T_3$ of the change in temperature of the interior, as indicated by the known temperature probe, and the curve $T_5$ applying for the interior of the coupling device 5.

On the other hand FIG. 3 shows the corresponding curves $T_3'$ and $T_5'$ applying for a device in accordance with the invention to indicate the more linear form of the curves as far as the point at which the desired sterilisation temperature is reached in the interior space.

We claim:

1. A device for the sterilization of a hose coupling device having two coupling halves in the connected condition thereof, comprising:
    a housing that is able to be opened and defining an interior space therein,
    at least two infrared radiation sources located in said interior space,
    a holding means for mounting the coupling device in the interior of the housing,
    a temperature probe positioned in the interior of the housing, and
    an automatic controller connected with the temperature probe and including means to set the temperature in the interior of the housing at a given value,
    said temperature probe having a reflective surface for reflecting infrared radiation and being heated substantially only by a convection air current.
2. The device as claimed in claim 1 wherein said infrared radiation sources comprise halogen lamps.
3. The device as claimed in claim 1 wherein said temperature probe further comprises a reflective surface for reflecting at least 75% of infrared radiation incident upon it.
4. The device as claimed in claim 1 wherein said temperature probe further comprises a reflective surface for reflecting at least 86% of infrared radiation incident upon it.
5. The device as claimed in claim 1 wherein said temperature probe includes a metallic layer adapted to reflect infrared radiation.
6. The device as claimed in claim 1 wherein said housing has an inner wall surface defining said cavity, the inner wall surface being adapted to reflect infrared radiation.
7. The device as claimed in claim 1 wherein said housing has a metal-coated inner wall surface defining said cavity for reflecting infrared radiation.
8. A device for the sterilization of a closed hose coupling which is disposed within the interior of an openable housing, the device comprising: at least two infrared radiation sources located in said housing interior,
    a holding means for mounting said hose coupling in said interior of said housing,
    a temperature probe positioned in said interior of said housing below said hose coupling, and
    a control means connected to said temperature probe for adjusting the temperature in the interior of said housing to a predetermined temperature,
    said temperature probe having a highly reflective outer surface for reflecting infrared radiation away from the probe without entering the probe, whereby the probe is heated essentially only by the convection of heated air.
9. A device according to claim 8 wherein said infrared radiation sources comprise halogen lamps.
10. A device according to claim 8 wherein said temperature probe reflective surface comprises a metal coating on the temperature probe.

* * * * *